United States Patent [19]

Mezrich et al.

[11] 4,298,009

[45] Nov. 3, 1981

[54] ULTRASOUND MAMMARY SCANNING APPARATUS

[75] Inventors: Reuben S. Mezrich, Miami, Fla.; David H. R. Vilkomerson, Princeton; Bayard Gardineer, Skillman, both of N.J.

[73] Assignee: Technicare Corporation, Solon, Ohio

[21] Appl. No.: 109,947

[22] Filed: Jan. 7, 1980

[51] Int. Cl.³ .............................................. A61B 10/00
[52] U.S. Cl. ..................................................... 128/660
[58] Field of Search ............................ 128/660–663; 73/618–629, 642, 644

[56] References Cited

U.S. PATENT DOCUMENTS

| | | | |
|---|---|---|---|
| 3,765,403 | 10/1973 | Brenden | 128/660 |
| 3,936,791 | 2/1976 | Kossoff | 128/660 X |
| 4,062,237 | 12/1977 | Fox | 128/663 X |
| 4,167,180 | 9/1979 | Kossoff | 128/660 |

FOREIGN PATENT DOCUMENTS 2919995  11/1979  Fed. Rep. of Germany ...... 128/660

OTHER PUBLICATIONS

Dick, D. et al., "High Resolution Rotating Head UTS Scanner", Intnl. Int. Publ. No.: WOX80/00193 (PCT), Feb. 7, 1980.

*Primary Examiner*—Robert W. Michell
*Assistant Examiner*—Francis J. Jaworski
*Attorney, Agent, or Firm*—Audley A. Ciamporcero, Jr.

[57] ABSTRACT

Ultrasound breast scanning and diagnosis is achieved by suspending the breast in a water pool, in which is immersed a wide aperture transducer/lens assembly. The water path is defined by two separate segments, an upper one, into which the breast is suspended, contained by a flexible sonically transparent bag member, and the lower being contained in a longitudinally movable tank which is filled to contact with the bag member portion protruding into the tank.

6 Claims, 7 Drawing Figures

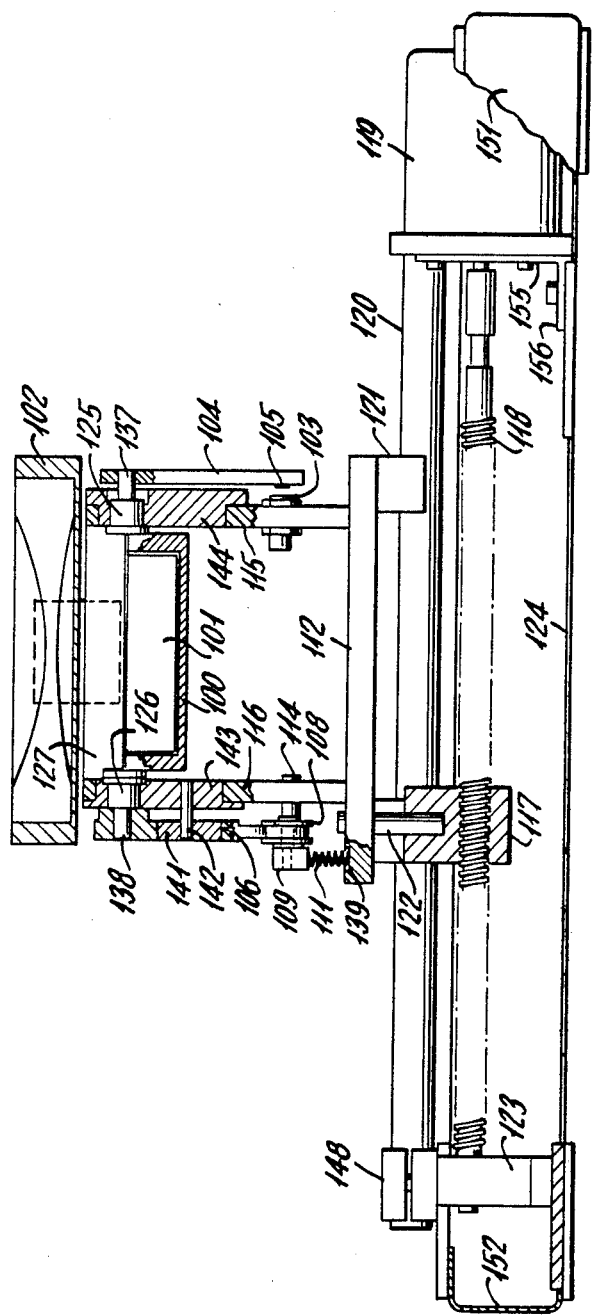

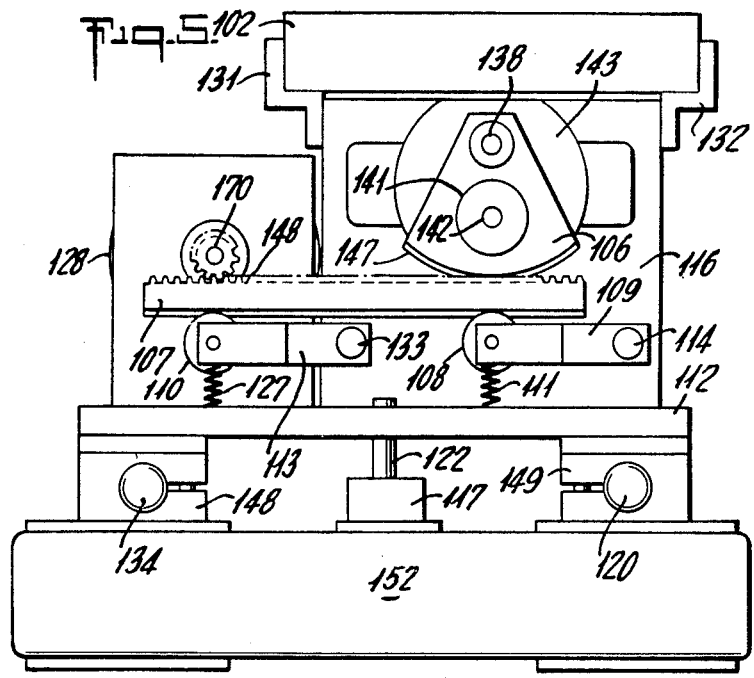
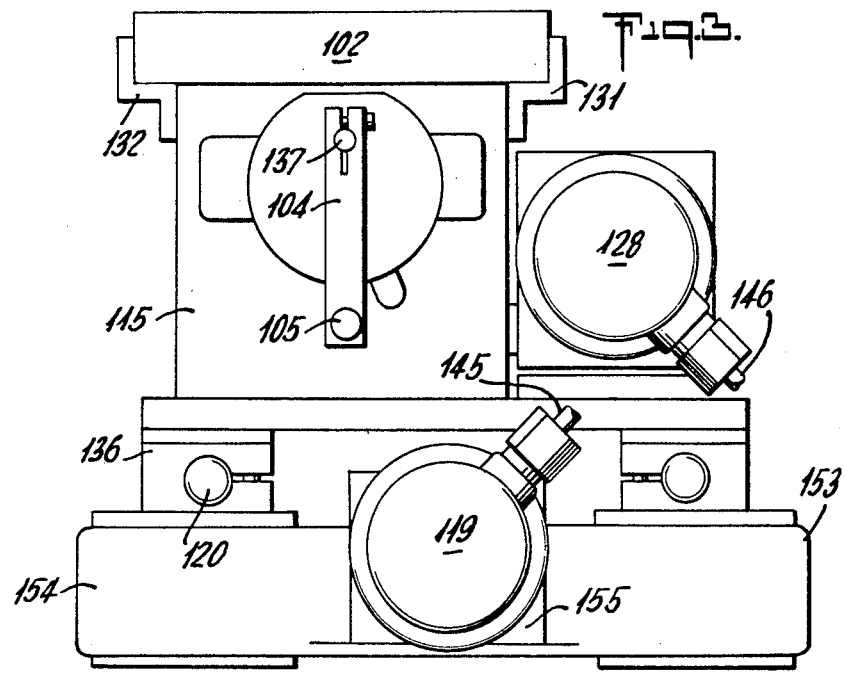

ULTRASOUND MAMMARY SCANNING APPARATUS

FIELD OF THE INVENTION

This invention relates to ultrasound imaging system, and more particularly to ultrasound imaging systems which are especially adapted to perform diagnostic and screening imaging of the human breast.

BACKGROUND OF THE INVENTION

Ultrasonic imaging has rapidly become a preferred modality for the non-invasive investigation of human tissues. Its non-ionizing character, moderate requirements in terms of signal processing and computation support, compactness, and, continuing progress in image quality, all mandate in favor of ultrasound whenever conditions permit. Thus, with the exception of body areas which are subject to uncontrolled multiple reflections (e.g. in the skull) and areas which fundamentally possess poor sonic transmission characteristics (e.g. the lungs), most body parts have been successfully made the subject of ultrasound diagnosis or screening. Some systems are multipurpose in essence, such as real time or B-scan body scanners and fetal monitors, while others are highly specialized, such as pulsed Doppler carotid imagers and flow monitors.

Recently, scientific and clinical data have been produced which provide strong indication of the efficacy of ultrasound scanning and imaging to screen, detect, and diagnose lesions in the human breast. In particular, it appears that appropriately directed and controlled B-scan images of a human breast permit detection of lesions in the 1 to 2 millimeter range and discrimination of malignancies in the 5 millimeter range based solely on ultrasound image. Further such screening appears feasible at statistical levels of confidence comparable to those achieved through utilization of ionizing radiation (i.e. X-ray mammography). Such efficacy, together with ultrasound's apparent hazard free nature, makes ultrasound a likely preferred modality for large scale screening programs for early detection of breast cancer.

It is accordingly a primary object of the present invention to provide apparatus employing the principles of ultrasound pulse-echo imaging for the screening of the breast, and further to provide control mechanisms and image quality which permit diagnostic utilization in accordance with the level of skill in the art.

It is another object to provide such apparatus which is readily and efficiently adjustable to accommodate substantially all women, irrespective of body physique or breast size or shape.

It is yet a further object that machine adjustment be quickly and conveniently achieved whereby large numbers of women may be quickly and effectively scanned, thereby to minimize the per procedure cost, and to promote effective large scale screening programs.

SUMMARY OF THE INVENTION

The present invention is premised on utilization of large aperture pulse-echo ultrasound imaging techniques, of the sort set forth in U.S. Pat. No. 4,131,021 and 4,131,022 to Mezrich et al. Accordingly, a physically oscillating or "nodding" transducer and an associated sonic lens are submerged in water, and the subject is positioned with the breast downwardly depending into the water, whereby the sonic energy from the transducer is transmitted through water into the breast, as focused by the sonic lens, and echoes are transmitted back in similar fashion through the water path. In greater particular, the principles of the present invention relate to plural, mutually synergistic adjustment mechanisms whereby substantially all subjects, regardless of physique and breast size, may be efficiently, conveniently, and comfortably screened utilizing the large aperture, transducer and lens water path approach.

Optionally, the subject addresses the instrument in a standing or kneeling posture, but in either event the upper portion of the body addresses the instrument in a prone or horizontal fashion, with the breast being suspended downwardly into a first pool of water. This first pool, which is defined by a flexible, sonically transparent bag member, provides physical isolation from the balance of the imaging apparatus. The body of the subject is positioned on a given axis, below which a tank is adjusted by movement in parallel with the axis, thereby to position the transducer-lens combination below the breast. The tank contains a second pool which carries the imaging apparatus and which forms a complete water path to the breast. More particularly, the transducer nods or oscillates, beneath a fixed lens, on an axis perpendicular to the axis of the torso of the subject. The whole apparatus carrying the transducer and lens is slowly moved transversely to the torso, whereby transducer oscillations produce separate B scan images of the breast, and successive lateral movements of the carriage provide successive adjacent scans. In a preferred form, the entire instrument is vertically adjustable, and a television camera is provided for correlating visually the exterior of the breast with cross-sectional scans thereof.

DESCRIPTION OF THE DRAWINGS

FIGS. 2 through 5 show respective view of a large aperture, transducer and lens mechanism adapted to operate in the context of the embodiment of FIG. 1.

BEST MODE FOR CARRYING OUT THE INVENTION

Figure 1:
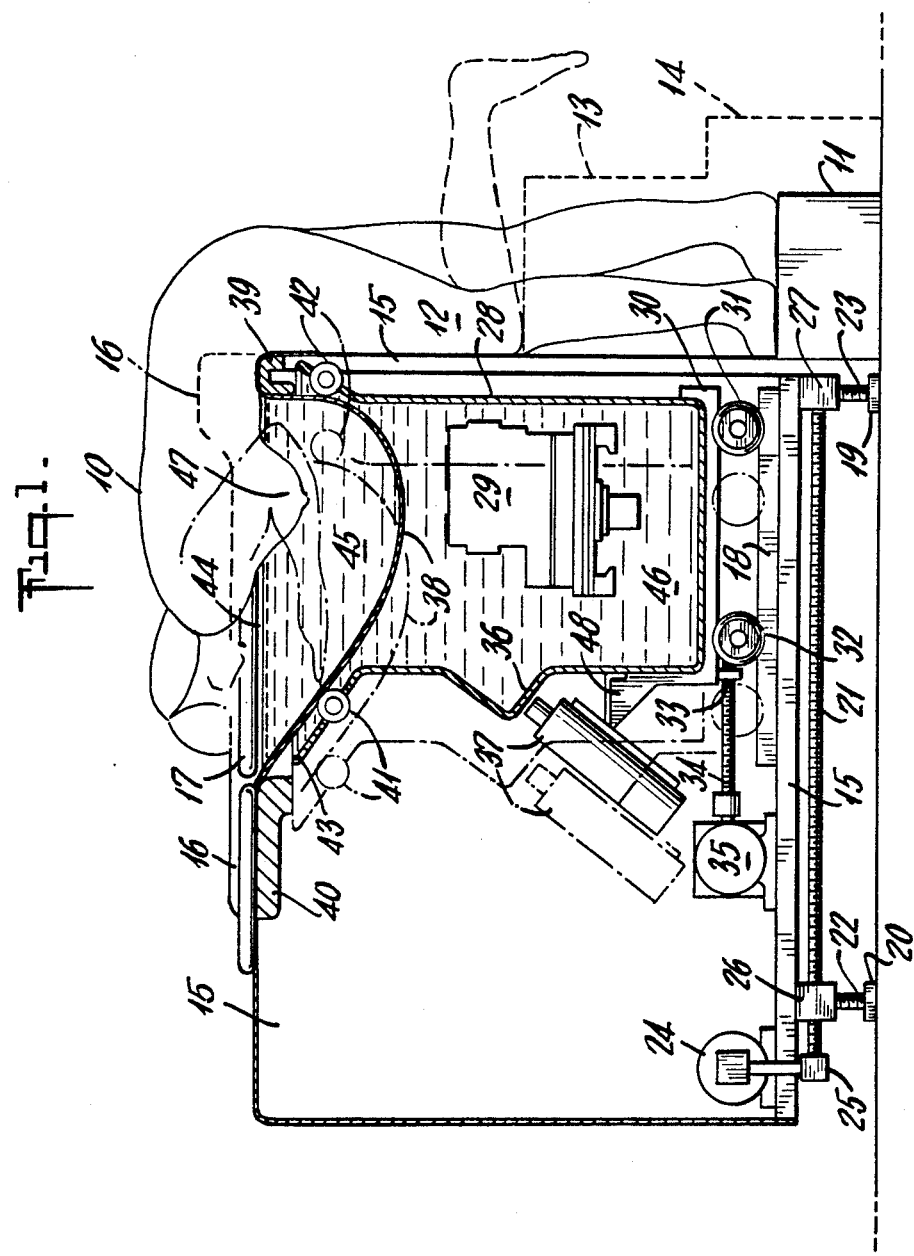
FIG. 1 shows a cross-sectional schematic of a preferred embodiment of the principles of the present invention.

Referring first to FIG. 1 there is shown a preferred embodiment of the principles of the present invention. In FIG. 1, a subject 10 is shown standing on a platform 11 with the thigh area 12 in a generally erect posture, the body bent at the hips, and the upper body or torso in a horizontal or prone position. As is noted in phantom, an optional approach is to utilize kneeling posture, incorporating a step 14 and kneeler 13, which may be preferable for some physiques, or more comfortable for some women. In either event, a cushion 16 and pillow 17 are provided suitably to locate the body (i.e. the longitudinal axis of the torso) on a particular axis of the instrument, which axis is parallel to the transducer B scan plane, and transverse to the progressive sectioning achieved by multiple adjacent sequential images.

The frame or chassis 15 is seen to be supported by foot pad members 19 and 20, which are height adjustable with respect to support blocks 26 and 27. As is shown symbolically in the drawing, a motor and transmission unit 24, differential 25, and screw/shaft 21 provides a system whereby the chassis 15 is appropriately raised or lowered so that the subject 10 comfortably may engage the cushion 16 and pillow 17, thereby to be properly positioned for imaging and screening. Not shown in FIG. 1 but well within the capability of those of ordinary skill in the art are the gear/translation mechanism in blocks 25, 26, and 27 to translate the rotational motion at motor 24 into vertical (e.g. screw) motion at 22 and 23.

A pair of rails 18 is carried within and upon the frame 15, and in turn, a carriage or trolley 30 rides thereupon. As shown in FIG. 1, wheels 31 and 32 ride on track 18 to translate the carriage 30, and in turn to translate the tank 28. A motor and gear box 35 turn a screw/shaft 34 through a fixed nut 33 attached to trolley 30 in order to achieve this translation.

Figure 6:
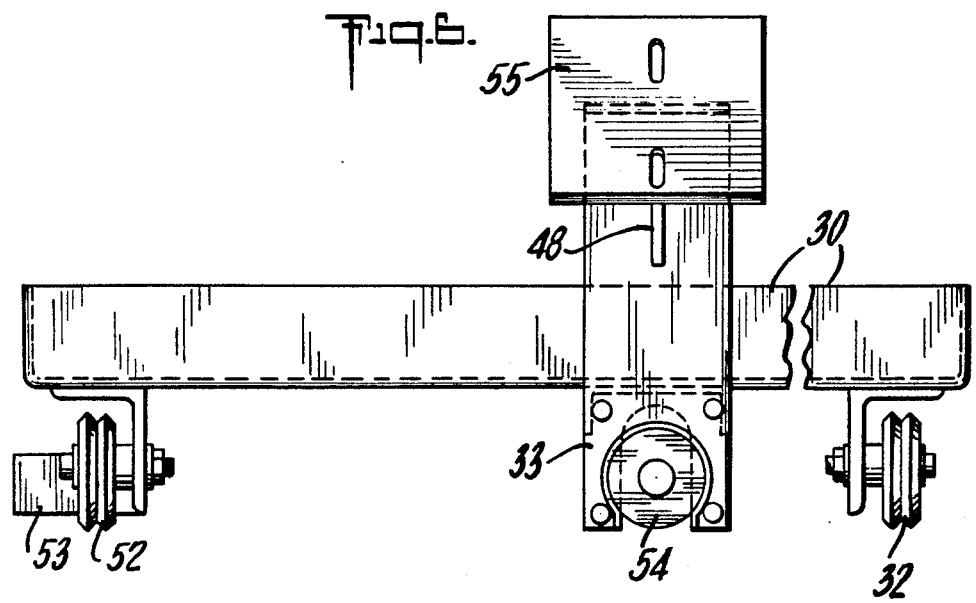
FIGS. 6 and 7 shows a preferred embodiment of a trolley mechanism operable in conjunction with the embodiment of FIG. 1.
Figure 7:
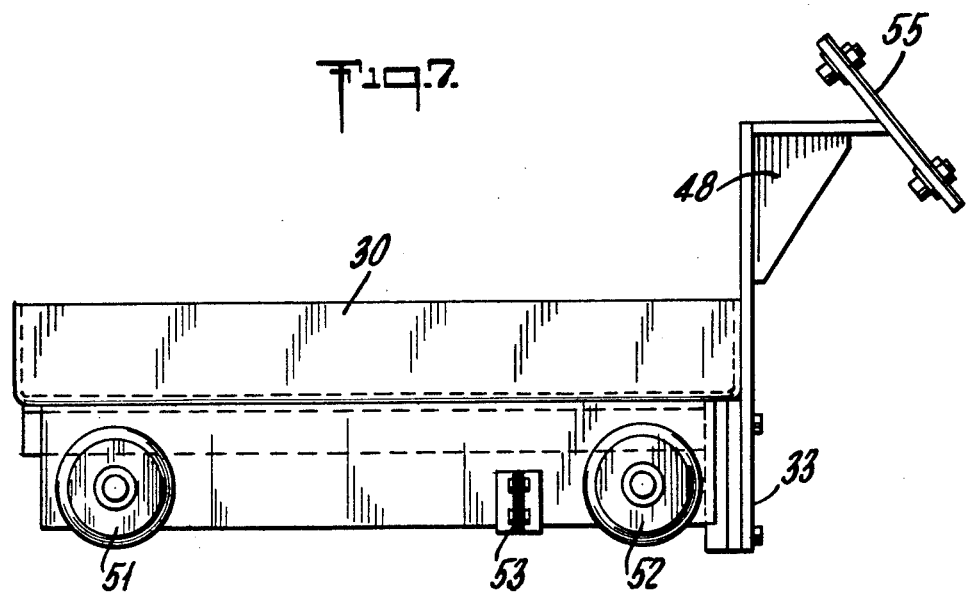

Greater detail with respect to the trolley 30 may be apprehended from FIGS. 6 and 7, which respectively show front and side views thereof. It will be noted that the leftward portion of the FIG. 6 front view is depicted in scale with the remaining portions thereof, but that the right side has been foreshortened for the sake of convenience. In FIGS. 6 and 7, wheels 32, 51, and 52 are evident, as is the particular construction of the nut 33 and 54 through which the screw 34 passes. Also evident in the foreground is an upward support member 48 and platform 55, to which may be affixed a television camera 37 as shown in FIG. 1. Also notable in FIGS. 6 and 7, but not evident from FIG. 1, is a protuberant bumper 53 useful in conjunction with the frame 15 itself to limit travel of the carriage 30.

Returning to FIG. 1, it will be seen that the carriage 30 bears a rigid tank 28 which is filled with water and which carries in the water an ultrasound scanning mechanism 29. The mechanism 29 is shown in considerable detail in FIGS. 2 through 5, and discussed in conjunction therewith. The tank 28 has outwardly sloping surfaces at the top, which suitably carry rollers 41 and 42 to facilitate sliding motion against a bag member 38, as the tank 28 is translated back and forth with carriage 30. A protuberance on the front of tank 28 carries a transparent window 36, through which a television camera 37 monitors the position of the breast 47 of the subject 10. Based upon the direct viewing of breast 47 by camera 37, tank 28 may be suitably placed with the scanning mechanism 29 disposed directly below the breast 47, for imaging thereof.

As may be noted from FIG. 1, the breast 47 of the subject 10 protrudes through an opening in the cushion 16, and extends downwardly into a first pool of water 45 contained by a flexible, sonically transparent bag member 38. The bag member 38 is affixed to the chassis 15 beneath the cushion 16 and secured about fixed members 39 and 40. Hence, as the water level is established at 44, the bag member 38 forms a pool 45, and to the extent permitted by the cross section of tank 28, extends downwardly therein. Correspondingly, tank 28 maintains a second pool of water 46 which fills the tank 28 and makes contact with the lower surface of bag member 38. Accordingly, there is established a reflection free path for sonic energy to pass from scanner 29 to the breast 47, and for echo signals to return from the breast 47 to the scanner 29.

The operation of tank 28 in conjunction with bag member 38 may be appreciated by considering the full lined drawing of those members, and the phantom drawings thereof. In particular, the full lined embodiment of FIG. 1 shows the tank 28, and carriage 30, near one extremity of travel. The phantom lined drawing shows the tank 28 and trolley 30 near the opposite extent of travel. It will be noted that as the tank 28 is so moved, the bag member 38 freely deforms, in cooperation with the slanted top portions of the tank 28 and the rollers 42. Depending, therefore, upon the physique of the subject 10, and therefore the lateral positioning of breast 47 in the first pool 45, the tank 28 may be appropriately positioned with the scanning mechanism 29 located directly below the breast tissue to be imaged.

Referring generally to FIGS. 2-5, there is shown an ultrasound scanning apparatus which employs the principles of the present invention. In particular, the apparatus set forth in various views in FIGS. 2-5 constitutes a mechanism adapted to be immersed in tank 28 into which the breasts of a patient are serially immersed above the scanning mechanism. For each breast, a series of B-scan "slices" are taken, across the breast, thereby yielding a comparable series of images which may be reviewed appropriately to identify lesions or suspicious tissue conditions within the breast.

The apparatus shown in FIGS. 2-5 is of the general class described in U.S. Pat. No. 4,131,021 of Mezrich et al. entitled "HIGH RESOLUTION PULSE ECHO ULTRASONIC IMAGING DISPLAY SYSTEM", and in a series of related companion patents to Mezrich et al. Generally, the Mezrich et al. series describe pulse echo ultrasound systems which employ a sonic lens intermediate the transducer and the patient. In such systems, the lens itself has a fixed aperture, typicaly by positionally fixing the lens, and the scanning of the ultrasound beam through a plane of tissue in interest occurs by manipulation of the beam on the side of the lens opposite the patient. In the embodiment of FIGS. 2-5, the lens itself is immersed in the water path, and the scanning takes place by means of physical oscillation of the transducer through a predetermined arc, typically in the range of thirty degrees. Inasmuch as the focal region of convergence of the lens has a finite depth, each transmission (and reception) of ultrasound pulses at a given position of the transducer yields an A-scan of the tissue within that focal region of convergence. Each half-cycle of oscillation of the transducer, then, results in a collection A-scan data, which is processed as is known in the art into a complete B-scan picture. In accordance with the embodiment of FIGS. 2-5, an entire carriage or mechanism bearing both the lens and the oscillating or "nodding" transducer is moved transversely below the tissue in interest (i.e. the breast suspended in water above the lens), to assemble a collection of B-scan "slices" which in the aggregate define the full three dimensions of the breast.

Referring with greater particularity to FIGS. 2-5, a base defined by members 151, 152, 153, and 154 lies fixed within the tank 28 beneath the location of the breast to be imaged. A motor 119, preferaby a stepping motor energized by electrical pulses provided via cable 145, is fixedly carried on the base by means of plates 155 and 156, to drive a threaded shaft 118, which at its other extreme is carried on a bearing 123. A pair of parallel support rails 120 and 134 extend along the length of the support base, rail 120 being rigidly mounted at its extremes on support blocks 149 and 136, and rail 134 being rigidly mounted at its extremes on support blocks 148 and 135. A carriage which bears the sonic transducer and lens assembly rides on rails 120 and 134, and is moved along those rails by engagement of block 117 with the threaded shaft 118. In turn, block 117 is rigidly connected to the carriage by means of a vertical connecting rod 122.

The carriage defining the ultrasound scanning assembly, which in its entirety is translated along rails 120 and 134 under the power of stepping motor 119, is principally defined by a base member 112 and vertical support side walls 115 and 116. Further, yet another stepping motor 128 is affixed to base member 112 by virtue of vertical mounting plate 129, whereby the stepping motor 128 is integral with the ultrasound scanning carriage, and is moved back and forth on rails 120 and 124 in conjunction therewith. The stepping motor 128, which is energized by signals furnished at cable 146, provides the reciprocal or oscillating motivation for a nodding ultrasound transducer 101, and thereby for generation of each B-scan frame through a collection of respective A-scan pulse-echo combinations emitted from the transducer 101. A sonic lens 102 is rigidly mounted to upright side walls 115 and 116 by transverse brackets 131 and 132. The transducer 101 itself is carried by a bracket 100, which by shaft members 137 and 138 and bearings 125 and 126, pivotably engages plate mountings 143 and 144. In turn, the plate mountings 143 and 144 are respectively attached to the side walls 115 and 116, thereby to mount the transducer 101 pivotally below lens 102, the pivoting occurring on the axis of shafts 137 and 138.

Figure 4:
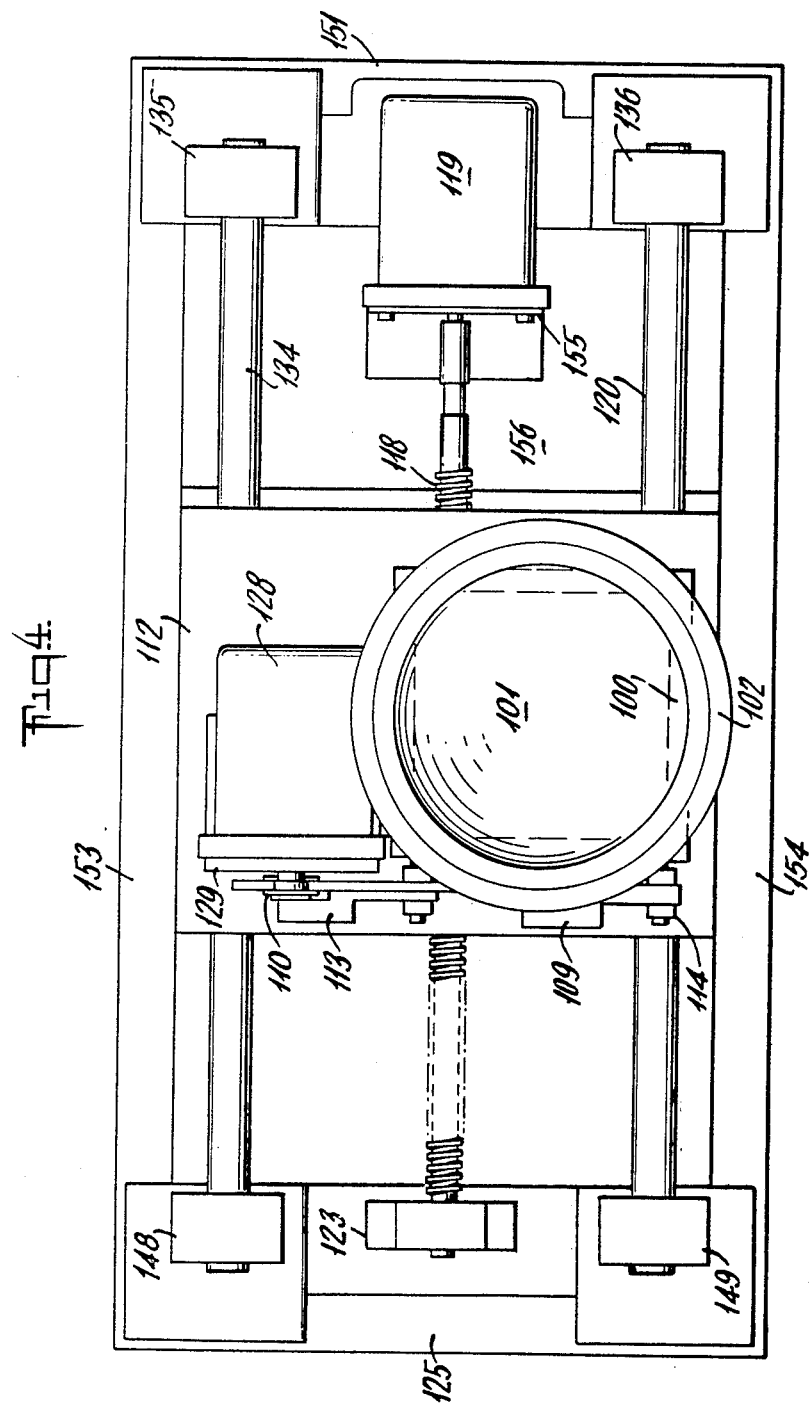

The pivoting transducer 101 may be seen from FIGS. 2, 4 and 5 to be interconnected with the stepping motor 128 by means of a drive gear 170, a rack 107, and a gear sector 106 which is attached to the shaft 138 of transducer bracket 100. As will be noted, the rack 107 is carried on spring loaded "slippers" or rollers 108 and 110, thereby tightly to engage an upper, toothed surface 148 of the rack 107 against correspondingly toothed and engaging gear 170 and the lower toothed portion 147 of gear sector 106. In particular, roller 110 is carried at one extreme of pivot arm 113, which pivots about bolt 133 and is loaded upwardly by spring 127. Similarly, roller 108 is carried at one extreme of lever arm 109, which is pivoted about bolt 114 and is loaded upwardly by spring 111. As will be noted by the partial cutaway in FIG. 2, spring 111 is held by natural tension in a depression 139 in the base plate 112. Spring 127 is similarly mounted in its own depression in base plate 112 (not shown). In a preferred embodiment, gear 170 and gear sector 106 are metallic in construction, whereas the rack 107 is made of a plastic material. The loading of rollers 110 and 108 beneath the mesh points of the rack 107 with gears 170 and 106 prevents gear backlash.

As may be noted most clearly in FIGS. 2 and 3, shaft 137 of transducer bracket 100 protrudes outwardly from plate 144 in wall 115, and rigidly connected thereto is a downwardly depending arm 104. At the lower terminus of arm 144 is mounted a magnet 105.

As will be best noted from FIG. 2, a commercially available Hall effect switch 103 penetrates and is rigidly mounted to support member 115 advantageously, at the midpoint of the arc travelled by magnet 105 as it moves in conjunction with oscillation of the transducer 101. Hence, the magnet 105 is aligned with the switch 103 once during each half-cycle of oscillation of the transducer 10. The Hall effect switch 103 is of common commercial pedigree, and operates to produce a pulse each time the field generated by magnet 105 is adjacent to (i.e., aligned with) the outer surface of the switch 103. Such pulses are useful to coordinate transmission, receipt, and display of data.

In partial summary, the apparatus of FIGS. 2-5 represents an immersible carriage and track assembly wherein the carriage holds an acoustic lens and a nodding transducer, as well as stepping motor and linkage apparatus for oscillating that transducer back and forth through a predetermined arc. An extension arm rocks along with the transducer, whereby a Hall effect switch senses occurrence of passage of a magnet at the end of the arm. The entire carriage is moved, transversely to the direction of oscillation of the transducer, along a track, thereby to enable irradiation of plural parallel planes in the tissue, and assembly of a corresponding plurality of B-scan images of the tissue under examination. The apparatus of FIGS. 2-5 is also disclosed in U.S. Application Ser. No. 100,598 of Gardineer et al, entitled "Transducer Drive and Control in Ultrasound Imaging Systems".

It will be appreciated that the above sets forth preferred and illustrative embodiments of the present invention, but that numerous alternative embodiments will occur to those of ordinary skill in the art without departure from the spirit or scope from the principles of the present invention.

What is claimed is:

1. A system employing sonic energy to derive select ones of a plurality of substantially parallel sectional images of the human breast of a subject comprising:
   (a) a frame member adapted at one extremity to receive the subject having the upper body generally prone, parallel to, and at least partially supported by a top surface of said frame member, said frame member defining a void in said top surface to receive the breast area of the subject;
   (b) means associated with said frame member for locating the prone upper body of the subject along a given axis;
   (c) a first sonically conductive fluid pool beneath and generally filling said void, said first pool being contained by a flexible, sonically transparent bag member suspended from said top surface, thereby to receive the breast area of the subject in said first pool;
   (d) a second sonically conductive fluid pool contained by a rigid tank, beneath said first pool, the open top of said bag member being larger in horizontal section than is said tank, said bag member being partially deformed downwardly into said tank by said first pool, said second pool filling said tank to contact the lower surface of said bag member;
   (e) first carriage means for carrying and translating said rigid tank relative to said frame member and to said bag member in a direction parallel to said given axis;
   (f) ultrasound transceiver means including
      (i) transducer means which oscillates about an axis normal to said given axis, and
      (ii) sonic focusing means intermediate said transducer means and said subject; and
   (g) second carriage means for carrying and translating said transciever means within said tank in a direction normal to said given axis.

2. A system as described in claim 1 and further including pedestal means upon which the subject may address said frame member in a kneeling posture.

3. A system as described in claim 2 and further including pedestal means upon which the subject may address said frame member in a standing posture.

4. A system as described in claim 1 and further including camera means for monitoring the position of the breast of the subject in said first pool, thereby providing a reference for controlling said first and second carriage means to position said tank and said transceiver for imaging specified sections of said breast.

5. A system as described in claim 4 wherein said tank includes an optically transparent window along one side thereof, and wherein said camera is carried on the outside of said tank adjacent said window.

6. A system employing sonic energy to derive sectional images of the human breast comprising:
   (a) a frame adapted at one extremity to receive a subject being generally erect in the thigh region, bent at the hips, and having the upper body generally prone, and parallel to and at least partially supported by a top surface of said frame member, said frame member defining a void in said top surface to receive the breast area of the subject;
   (b) means associated with said frame member for locating the prone upper body of the subject along a given axis;
   (c) a first sonically conductive fluid pool beneath and generally filling said void, said first pool being contained by a flexible, sonically transparent bag member suspended from said top surface, thereby to receive the breast region of the subject in said first pool;
   (d) a second sonically conductive fluid pool contained by a rigid tank, beneath said first pool, the open top of said bag member being larger in horizontal section than is said tank, said bag member being partially deformed downwardly into said tank by said first pool, said second pool filling said tank to contact the lower surface of said bag member
      (i) wherein said tank includes an optically transparent window along one side thereof, and
      (ii) wherein said tank includes roller means along its top edges to facilitate translation of said tank relative to said bag member; and
   (e) first carriage means for carrying and translating said rigid tank relative to said frame member in a direction parallel to said given axis;
   (f) ultrasound transceiver means including
      (i) transducer means which oscillates about an axis normal to said given axis, and
      (ii) sonic focusing means intermediate said transducer means and said subject;
   (g) second carriage means for carrying and translating said transceiver means within said tank in a direction normal to said given axis; and
   (h) camera means for monitoring the position of the breast of the subject in said first pool, thereby providing a reference for controlling said first and second carriage means to position said tank and said transceiver for imaging specified sections of said breast, and wherein said camera means is carried on the outside of said tank adjacent said window.

* * * * *